(12) United States Patent
Passmore

(10) Patent No.: US 6,923,816 B1
(45) Date of Patent: *Aug. 2, 2005

(54) MEDICAL SKIN-MARKING DEVICE

(76) Inventor: Jay Passmore, 42 W. Pleasant St., Westbrook, ME (US) 04092

( * ) Notice: Subject to any disclaimer, the term of this patent is extended or adjusted under 35 U.S.C. 154(b) by 136 days.

This patent is subject to a terminal disclaimer.

(21) Appl. No.: 10/178,460

(22) Filed: Jun. 24, 2002

Related U.S. Application Data

(62) Division of application No. 09/687,580, filed on Oct. 14, 2000, now Pat. No. 6,436,105.

(51) Int. Cl.7 ............................................. A61B 17/00

(52) U.S. Cl. .................................................... 606/116

(58) Field of Search ...................... 606/116, 117–131, 606/181, 184, 185, 186, 187

(56) References Cited

U.S. PATENT DOCUMENTS

| | | | | |
|---|---|---|---|---|
| 4,572,831 | A | * | 2/1986 | Rosen ......................... 606/116 |
| 5,496,304 | A | * | 3/1996 | Chasan ........................ 606/116 |
| 5,810,862 | A | * | 9/1998 | Pilmanis ...................... 606/186 |
| 6,197,034 | B1 | * | 3/2001 | Gvozdic et al. ............. 606/116 |
| 6,685,719 | B2 | | 2/2004 | Matera, Jr. |

* cited by examiner

Primary Examiner—Kevin T. Truong
(74) Attorney, Agent, or Firm—Patricia M. Mathers; Thomas L. Bohan

(57) ABSTRACT

A sterile, disposable skin-marking device for applying a marking agent to the skin of a patient who is to undergo radiation therapy. The skin-marking device has a short single needle attached to the operating end of the device and a flexible housing that contains a rupturable cartridge of marking agent. When the cartridge is ruptured by flexing or compressing the housing, the marking agent flows into the needle, which is then used to penetrate the skin of the patient and mark treatment set-up points on the skin by applying the marking agent to the skin.

2 Claims, 1 Drawing Sheet

MEDICAL SKIN-MARKING DEVICE

This application is a divisional of U.S. patent application Ser. No. 09/687,580, filed on Oct. 14, 2000, now U.S. Pat. No. 6,436,105 which is hereby incorporated herein by reference.

BACKGROUND INFORMATION

1. Field of the Invention

The invention relates to the field of marking an area on the body of a patient as a guide for medical treatment. More particularly, the invention relates to marking the skin of a patient in preparation for medical treatment. Most particularly yet, the invention relates to applying marks to the skin of a patient undergoing radiation therapy.

2. Description of the Prior Art

Markings, also often referred to as tattoos, are typically applied to the skin of a patient in preparation for radiation therapy or other medical treatment, as a means of clearly delineating the location of treatment set-up points. Traditionally, the marking is done by applying a drop of marking agent to the surface of the patient's skin and then penetrating the skin with a needle to allow the marking agent to flow under the surface of the skin. The size of the needle used can vary widely, some technicians preferring to work with a larger needle, others with a smaller needle. When marking the skin in this way, it is critical that the marking agent, such as India ink, as well as the needle tip be sterile. Furthermore, it is highly desirable to have a disposable needle, to eliminate the possibility of passing pathogens from one person to another and to eliminate the need for sterilizing the needles. It is also desirable to have a marking device that will accept a standard needle that is typically kept in stock in a healthcare facility, in a range of needle gauges.

Sarath et al. (U.S. Pat. No. 4,798,582; 1989) discloses a needle cartridge that is threadably mounted onto the drive shaft of an electrical tattooing instrument. Chasan (U.S. Pat. No. 5,496,304; 1996) discloses a surgical marking pen for drawing lines on the skin of a patient. The Chasan device has a handle and a fluid reservoir that communicates with a pinwheel that penetrates the skin. Arranged around the circumference of the pinwheel is a plurality of needle tips that puncture the skin, leaving a tattooed line in the epidermis of the skin. The marking pen disclosed therein may be disposable, or refillable. The disadvantages of these devices are that they require special equipment or special needles. The device disclosed in Chasan has the further disadvantage of not being suited for placing individual circular or triangular markings on the skin, that is, it is a device that draws lines, rather than marks points.

Rosen (U.S. Pat. No. 6,056,737; 2000) discloses a disposable skin-marking device that is provided in a sealed sterile package and is discarded after a single use. The skin-marking device has a felt-tip nib and includes a glass cartridge containing marking agent inside a flexible housing. The cartridge is ruptured by bending or compressing the housing, whereupon the marking agent flows into the nib of the pen. This type of device is not suited to applying a marking agent under the surface layer of the skin.

Therefore, what is needed is a skin-marking device for applying a marking agent beneath one or more layers of the skin. What is further needed is such a device that provides a sterile supply of the marking agent and is disposable after a single use. What is still further needed is such a device that accepts a standard general-purpose needle in a range of needle gauges.

SUMMARY OF THE INVENTION

For the above cited reasons, it is an object of the invention to provide a disposable sterile skin-marking device that carries a cartridge of sterile marking agent and uses a needle to apply the marking agent beneath one or more layers of the skin surface. It is a further object of the invention to provide such a skin-marking device that will accept a standard needle in a range of needle gauges.

The object of the invention is achieved by providing a skin-marking device that has a flexible housing provided with a quick-coupling type of coupler that is adapted to receive a needle provided with a base that mates with the quick-coupler on the housing. In the Preferred Embodiment, the quick-coupler is a LUER-LOK type coupler and the housing has a female coupler and the needle base a male coupler. Any one of a range of needles provided with a LUER-LOK type base can be inserted into the needle end of the skin-marking device. Alternative embodiments may include other types of standard coupling mechanisms that are typically provided on needles supplied to healthcare facilities. Thus, needles in a range of needle gauges are available to the technician preparing the patient for the radiation therapy and he or she can choose the preferred needle size. The device is supplied packaged in sterile, protective material.

The flexible housing contains a sealed rupturable cartridge that contains sterile marking agent, such as India-ink. The cartridge is ruptured by flexing or compressing the housing, while the needle sheath is still intact and in place. The marking agent flows into the needle and, after removing the sheath, the needle is used to penetrate the skin of the patient to apply the marking agent. The cartridge contains sufficient marking agent to apply multiple tattoos to a single patient. The entire device including needle is discarded after use.

The skin-marking device is provided as a sealed, sterile unit that includes the housing, the cartridge with marking agent, a seal cap at the end of the housing, a LUER-LOK tip for receiving a needle, and a LUER-LOK cap to seal the needle end of the skin-marking device before use. When ready to apply the tattoo to the patient, the LUER-LOK cap is removed, a needle with a LUER-LOK base is fitted into the LUER-LOK tip of the device, and the housing flexed to rupture the sealed cartridge with the marking agent. The marking agent flows into the needle, and the technician can now remove the needle sheath and apply the marking agent beneath one or more layers of the skin to precisely mark the location for treatment setup.

In a first alternative embodiment, the quick-coupler on the housing of the skin-marking device is provided with a needle tip that is short enough that a needle with a base that mates with the quick-coupler may be fitted over the short needle. This is an advantage in that the skin-marking devices may be provided with a typical gauge needle tip for skin-marking, but a technician who has a preference for a longer needle or a different gauge needle may attach the preferred needle to the skin-marking device without having to remove the short needle tip.

In a further alternative embodiment of the present invention, the skin-marking device can be supplied as a disposable, ready-to-use unit that includes a flexible housing with a cartridge of sterile skin-marking agent, without a quick-coupler, and already fitted with a standard gauge needle for skin-marking.

DETAILED DESCRIPTION OF THE PREFERRED EMBODIMENT

Figure 1:
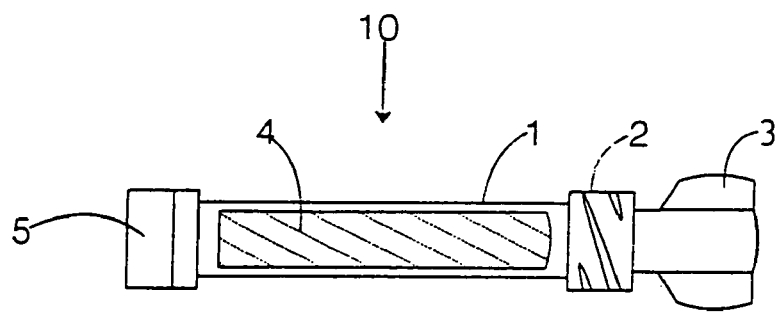
FIG. 1 shows the skin-marking device of the present invention as it is provided to the healthcare facility that applies the marking agent.

FIG. 1 shows the preferred embodiment of a skin-marking device 10 according to the present invention. The skin-marking device 10 comprises a flexible housing 1, a LUER-LOK coupler 2, a LUER-LOK seal cap 3, a sealed cartridge 4 containing sterile marking agent, such as India-ink, and an end seal cap 5. In the Preferred Embodiment, the LUER-LOK seal cap 3 and the end seal cap 5 are plastic caps that snap onto the respective ends of the housing 1 to effectively seal the cartridge in the housing 1. The LUER-LOK coupler 2 is adapted to receive a needle 6 (shown in FIG. 2) or other device that has a LUER-LOK base that mates with the LUER-LOK coupler 2.

Figure 2:
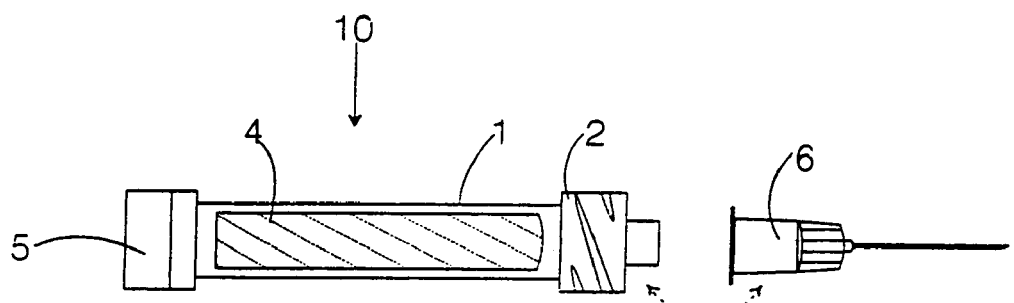
FIG. 2 shows the skin-marking device being readied for an application of the marking agent to the skin of a patient.

FIG. 2 shows the Preferred Embodiment of the skin-marking device 10 being readied for an application of marking agent. As can be seen, the LUER-LOK seal cap 3 has been removed from the skin-marking device 10. For purposes of illustration, the needle 6 with a LUER-LOK base has already been removed from a protective, sterile-seal sheath (not shown) and is ready to be inserted into the LUER-LOK coupler 2 of the skin-marking device 10.

The technicians who apply the skin markings to the patients may have a preferences for a particular size needle. Typically, the particular treatment facility will stock needles 6 having a LUER-LOK base in a range of sizes, to be used for a variety of different applications. The particular technician applying the skin-marking selects his or her preferred needle size, fits the needle 6 onto the skin-marking device 10, flexes or compresses the flexible housing 1 while the needle sheath is still in place to rupture the sealed cartridge containing the marking agent, and then removes the sheath to apply the marking agent to the desired location on the skin of the patient. The needle 6 is a conventional needle that is typically supplied to health care facilities, enclosed in a rigid, sterile protective sheath that has a seal that is broken before use. Since the needle 6 and its sheath is a conventional device, well-known in the field, and does not constitute the claimed novelty of the present invention, the needle is not shown in any detail in the FIGURES and the needle sheath is not shown at all.

Figure 3:
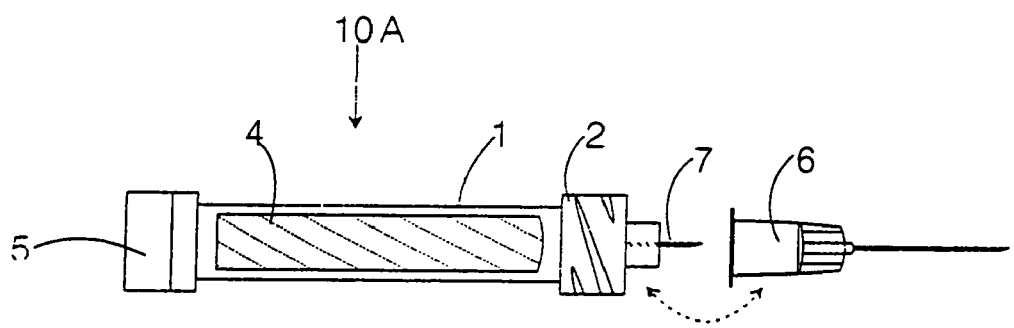
FIG. 3 shows a first alternative embodiment of the skin-marking device according to the present invention, having a short needle tip, over which a standard needle can be attached.

FIG. 3 shows a skin-marking device 10A that is a first alternative embodiment of the skin-marking device 10 according to the present invention. The same reference designations are used to identify components of the device 10A that are identical to the components of the skin-marking device 10. As can be seen, a short needle tip 7 is provided in the LUER-LOK coupler 2 of the flexible housing 1. A needle 6 that has a LUER-LOK base that mates with the LUER-LOK coupler 2 can be inserted into the LUER-LOK coupler 2, without first removing the short needle tip 7.

Figure 4:
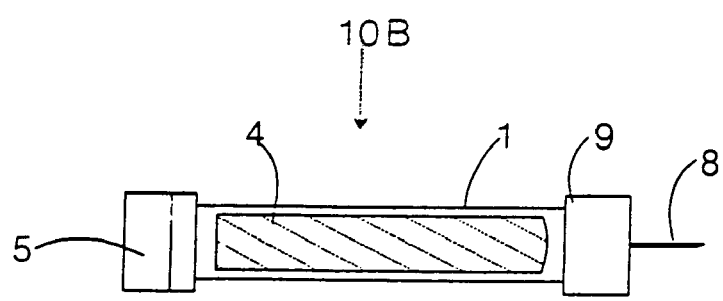
FIG. 4 shows a second alternative embodiment of the skin-marking device according to the present invention having a housing without a quick-coupler, and a fixed needle tip.

FIG. 4 shows a skin-marking device 10B that is a second alternative embodiment of the skin-marking device 10 of the present invention. Again, the same reference designations are used to identify components of the device 10B that are identical to components of the skin-marking device 10. In this second alternative embodiment, the skin-marking device 10B is provided as a ready-to-use, disposable skin-marking device that does not have a quick-coupler, but a fixed needle base 9, and is provided with a needle tip 8 that is a standard gauge needle for marking skin in preparation for treatment.

It should be understood that the embodiments mentioned herein are merely illustrative of the present invention. Variations in construction and use of the present invention may be contemplated in view of the following claims without straying from the intended scope and field of the invention herein disclosed.

What is claimed is:

1. A skin-marking device for applying a marking agent beneath a surface layer of the skin, said skin-marking device comprising:
   a plungerless, flexible housing having a first end and a second end;
   a rupturable cartridge of marking agent enclosed within said housing;
   a single, short needle tip, fixedly attached to said first end of said flexible housing, through which said marking agent is flowable.

2. The skin-marking device of claim 1, wherein said marking agent is deliverable through said needle tip by squeezing said housing when said cartridge is ruptured.

* * * * *